(12) United States Patent
Takano et al.

(10) Patent No.: US 6,753,330 B2
(45) Date of Patent: Jun. 22, 2004

(54) SOLID DISPERSION COMPOSITION

(75) Inventors: Niichiro Takano, Fuji (JP); Hiroyuki Kawashima, Fuji (JP); Yasuo Shinoda, Shizuoka (JP); Toshio Inagi, Mishima (JP)

(73) Assignee: Kowa Co., Ltd., Nagoya (JP)

( * ) Notice: Subject to any disclaimer, the term of this patent is extended or adjusted under 35 U.S.C. 154(b) by 0 days.

(21) Appl. No.: 10/414,008

(22) Filed: Apr. 16, 2003

(65) Prior Publication Data

US 2004/0019122 A1 Jan. 29, 2004

Related U.S. Application Data

(60) Provisional application No. 60/372,416, filed on Apr. 16, 2002.

(51) Int. Cl.[7] ............................................... A61K 31/50
(52) U.S. Cl. ........................................................ 514/247
(58) Field of Search ........................................... 514/247

(56) References Cited

FOREIGN PATENT DOCUMENTS

| JP | 2000-198776 | | 7/2000 |
|---|---|---|---|
| WO | WO 99/25697 | * | 5/1999 |

* cited by examiner

Primary Examiner—Raymond J. Henley, III
(74) Attorney, Agent, or Firm—Oblon, Spivak, McClelland, Maier & Neustadt, P.C.

(57) ABSTRACT

The invention provides a solid dispersion composition containing 2-benzyl-5-(4-chlorophenyl)-6-[4-(methylthio) phenyl]-2H-pyridazin-3-one, hydroxypropylmethyl cellulose, and polyoxyethylene polyoxypropylene glycol. The solid dispersion composition of the present invention exhibits the excellent dissolvability of 2-benzyl-5-(4-chlorophenyl)-6-[4-(methylthio)phenyl]-2H-pyridazin-3-one in water, and enables this compound to be constant sequentially and thereby improve absorbability in blood.

2 Claims, No Drawings

SOLID DISPERSION COMPOSITION

This application claims the benefit of U.S. Provisional Application Ser. No. 60/372,416, filed Apr. 16, 2002.

BACKGROUND OF THE INVENTION

1. Field of the Invention

The present invention relates to a solid dispersion composition containing 2-benzyl-5-(4-chlorophenyl)-6-[4-(methylthio)phenyl]-2H-pyridazin-3-one (hereinafter referred to as "compound 1"), which has excellent dissolvability and dissolution stability alike.

2. Background Art

Compound 1, which exerts an excellent effect for suppressing production of interleukin 1β, is known to be useful as a prophylactic and therapeutic agent for immunological diseases, inflammatory diseases, and ischemic diseases, particularly as a therapeutic agent for articular rheumatism (disclosed in Japanese Patent Application Laid-Open (kokai) No. 2000-198776).

The present inventors have conducted studies on use of the aforementioned compound 1 in a peroral pharmaceutical composition. However, compound 1 has exceptionally poor solubility in water, and its dissolvability from the pharmaceutical composition is very bad. Thus, such a composition proved impossible to satisfy sufficient pharmaceutical effects.

Generally, dissolvability in water of a poor water dissoluble drug in a pharmaceutical composition is known to be improved by micro-pulverization of the drug and/or transformation of the drug into a derivative thereof. However, in the case of compound 1, micro-pulverization does not work; i.e., dissolvability is not improved, and transformation into a derivative results in unwanted changes in pharmaceutical effect.

Accordingly, the purpose of the present invention is to enhance the dissolvability of compound 1 from a pharmaceutical composition and thus provide the pharmaceutical composition containing said compound, which has the excellent dissolution stability with allowing said compound to keep a constant concentration after dissolving from the composition.

SUMMARY OF THE INVENTION

The present inventors have prepared compositions containing compound 1 and a variety of other components and investigated dissolvability of compound 1 contained in these compositions, and have found that, when a dispersion composition in solid form (hereinafter referred to as a solid dispersion composition) is prepared from compound 1, hydroxypropylmethyl cellulose, and polyoxyethylene polyoxypropylene glycol, dissolvability of compound 1 can be remarkably enhanced; that the concentration of compound 1 can be constant after dissolving from the composition; and that a composition useful as a peroral pharmaceutical can be obtained from the solid dispersion composition. The present invention has been accomplished on the basis of these findings.

Thus, the present invention provides a solid dispersion composition comprising compound 1, hydroxypropylmethyl cellulose, and polyoxyethylene polyoxypropylene glycol.

In another aspect of the present invention, there is provided a readily dissoluble pharmaceutical composition comprising a solid dispersion composition containing compound 1, hydroxypropylmethyl cellulose and polyoxyethylene polyoxypropylene glycol, and a pharmacologically acceptable carrier.

DETAILED DESCRIPTION OF PREFERRED EMBODIMENTS

Compound 1 employed in the present invention; i.e., 2-benzyl-5-(4-chlorophenyl)-6-[4-(methylthio)phenyl]-2H-pyridazin-3-one, can be produced through any known method, such as a method disclosed in Japanese Patent Application Laid-Open (kokai) No. 2000-198776.

Preferably, the solid dispersion composition of the present invention contains compound 1 in an amount of 0.1–35 wt. %, more preferably 1–30 wt. %, particularly preferably 5–25 wt. %.

The hydroxypropylmethyl cellulose which is employed in the present invention has a methoxy group content of 19–30 wt. %, preferably 28–30 wt. %, and a hydroxypropoxy group content of 4–12 wt. %, preferably 7–12 wt. %. More preferably, the hydroxypropylmethyl cellulose has a viscosity of 2.5–7 mm$^2$/s (20° C.). As used herein, viscosity is that measured at 20° C. through a viscosity determination method 1 described in Japanese Pharmacopoeia (i.e., capillary tube viscometer method) by use of an aqueous solution in which a sample (2 g) is dissolved in water (98 mL). Specific examples include hydroxypropylmethyl cellulose 2208, hydroxypropylmethyl cellulose 2906, and hydroxypropylmethyl cellulose 2910; and, as commercial products, Metolose 90SH, Metolose 65SH, Metolose 60SH, TC-5E, TC-5R and TC-5S (product of Shin-Etsu Chemical Co., Ltd.); Metocel K, Metocel F, and Metocel E (product of Dow Chemical Co.); and Marpolose (product of Matsumoto Yushi-Seiyaku Co., Ltd.).

Preferably, hydroxypropylmethyl cellulose is incorporated in an amount of 2–15 parts by weight based on 1 part by weight of compound 1, particularly preferably 3–10 parts by weight.

Preferably, the polyoxyethylene polyoxypropylene glycol which is employed in the present invention has the mean degree of polymerization of ethylene oxide of 3–200, more preferably 54–196, particularly preferably 105–160, and the mean degree of polymerization of propylene oxide of 5–70, more preferably 5–40, particularly preferably 5–30.

Examples of polyoxyethylene polyoxypropylene glycol species include polyoxyethylene(105) polyoxypropylene(5) glycol, polyoxyethylene(120) polyoxypropylene(40) glycol, polyoxyethylene(160) polyoxypropylene(30) glycol, polyoxyethylene(196) polyoxypropylene(67) glycol, polyoxyethylene(20) polyoxypropylene(20) glycol, polyoxyethylene(200) polyoxypropylene(70) glycol, polyoxyethylene(3) polyoxypropylene(17) glycol, polyoxyethylene(42) polyoxypropylene(67) glycol, and polyoxyethylene(54) polyoxypropylene(39) glycol; and, as commercial products, PEP 101 (product of Freund Industrial Co., Ltd.); Adeka Pluronic F-87, Adeka Pluronic L-44, Adeka Pluronic F-68, and Adeka Pluronic L-31 (product of Asahi Denka Kogyo co., Ltd.); and Unilube, Unilube 40DP-40B, Unilube 70DP-950B, and Plonon (product of Nippon Oil & Fats Co., Ltd.). The parenthetic number refers to the mean degree of polymerization of ethylene oxide or propylene oxide.

Preferably, polyoxyethylene polyoxypropylene glycol is incorporated in an amount of 0.01–3 parts by weight based on 1 part by weight of compound 1, particularly preferably 0.1–1 parts by weight.

In a preferred mode, the three-component solid dispersion composition is produced by dissolving three components in a solvent and removing the solvent through the method as described hereinafter.

The solvent is selected on the solubility of these three components. Examples thereof include organic solvents such as methyl alcohol, ethyl alcohol, isopropyl alcohol, acetone, and dichloromethane; mixtures thereof; and mixtures thereof with water.

No particular limitation is imposed on the method of removing the solvent, and any method can be employed so long as the method enables removal of the solvent. Examples of the method include evaporation under reduced pressure; atomizing the solution by means of a spray dryer; and applying the solution to core particles (lactose, microcrystalline cellulose, anhydrous dibasic calcium phosphate, etc.) placed in an apparatus such as a fluid bed granulator or a rotary granulator, to thereby cause the solvent to be evaporated.

While the solid dispersion composition of the present invention is required to contain hydroxypropylmethyl cellulose and polyoxyethylene polyoxypropylene glycol, the effects of the present invention remain persistent even when other ingredients are added thereto.

From the standpoint of dissolvability of compound 1, the solid dispersion composition preferably has an average particle size of 1–1,000 $\mu$m, more preferably 2–800 $\mu$m, particularly preferably 10–600 $\mu$m. As used herein, the average particle size refers to an average particle size as measured through a laser beam scattering diffraction method.

The readily-dissoluble pharmaceutical composition of the present invention may serve either as a solid dispersion composition which has beforehand been prepared to comprise comopound 1, hydroxypropylmethyl cellulose and polyoxyethylene polyoxypropylene glycol, or as a readily-dissoluble pharmaceutical composition mixed in various forms with a pharmacologically acceptable carrier. For the present invention, the latter composition is preferred from the viewpoint of dissolvability.

Examples of the pharmacologically acceptable carrier include excipients such as lactose, microcrystalline cellulose, sucrose, mannitol, light anhydrous silicic acid, and dibasic calcium phosphate; binders such as methyl cellulose, hydroxypropyl cellulose, gelatin, polyvinylpyrrolidone, and pullulan; disintegrants such as croscarmelose sodium, carmellose calcium, cros povidone and low-substituted hydroxypropyl cellulose; lubricants such as magnesium stearate and talc; colorants such as tar pigments and red ferric oxide; and flavoring agents such as stevia, aspartame, and perfume.

No particular limitation is imposed on the form of the dissolution-facilitating pharmaceutical composition of the present invention, and any form is acceptable so long as it is a solid form. Examples of forms for easy ingestion include tablets, capsules, granules, and fine granules.

EXAMPLES

The present invention will be described in more detail by way of Examples and Comparative Examples, which should not be construed as limiting the invention thereto.

Example 1

Compound 1 (150 g), hydroxypropylmethyl cellulose (methoxy group content: 29 wt. %, hydroxypropoxy group content: 10 wt. %) (TC-5R, product of Shin-Etsu Chemical Co., Ltd.) (450 g), and polyoxyethylene(105) polyoxypropylene(5) glycol (PEP 101, product of Freund Industrial Co., Ltd.) (30 g) were added to an ethylalcohol/acetone/water mixture (proportions by volume: 9/10/1) (24 L) with stirring at 50° C., to thereby dissolve these ingredients. The thus-prepared solution was applied to lactose (300 g) placed in a fluid bed granulator, and granulation was performed, to thereby yield granules of a solid dispersion composition.

The average particle size of the granules, as measured by means of a particle size distribution measurement apparatus of laser beam scattering diffraction type (LS 230, product of Beckmann & Coulter), was found to be 327 $\mu$m. This method of measurement was also applied to the following Examples and Comparative Examples.

Example 2

The procedure of Example 1 was repeated, except that polyoxyethylene(160) polyoxypropylene(30) glycol (Adeka Pluronic F-68, product of Asahi Denka Kogyo Co., Ltd.) was used instead of polyoxyethylene(105) polyoxypropylene(5) glycol (PEP 101, product of Freund Industrial Co., Ltd.), to thereby yield granules of a solid dispersion composition (average particle size: 386 $\mu$m).

Comparative Example 1

Compound 1 (15 g), hydroxypropylmethyl cellulose (the same as used in Example 1)(45 g), and polyoxyethylene (105) polyoxypropylene (5) glycol (the same as used in Example 1)(3 g) were mixed together in a mortal, to thereby yield powder.

Comparative Example 2

Compound 1 (15 g) and hydroxypropylmethyl cellulose (the same as used in Example 1) (45 g) were added to an ethylalcohol/acetone/water mixture (proportions by volume: 9/10/1) (2400 mL) with stirring at 50° C., to thereby dissolve these ingredients. The thus-prepared solution was atomized by means of a spray dryer, to thereby yield a solid dispersion powder (average particle size: 21 $\mu$m).

Comparative Example 3

Compound 1 (15 g), hydroxypropylmethyl cellulose (the same as used in Example 1) (45 g), glyceryl monostearate (Nikkol MGS-B, product of Nikko Chemicals Co., Ltd.) (1.5 g), and polyoxyl 40 stearate (Nikkol MYS-40, product of Nikko Chemicals Co., Ltd.) (3 g) were added to an ethylalcohol/acetone/water mixture (proportions by volume: 9/10/1) (2400 mL) with stirring at 50° C., to thereby dissolve these ingredients. The thus-prepared solution was atomized by means of a spray dryer, to thereby yield a solid dispersion powder (average particle size: 18 $\mu$m).

Comparative Example 4

Compound 1 (15 g), hydroxypropylmethyl cellulose (the same as used in Example 1) (45 g), and polysorvate 80 (Nikkol TO-10M, product of Nikko Chemicals Co., Ltd.) (7.5 g) were added to an ethylalcohol/acetone/water mixture (proportions by volume: 9/10/1) (2400 mL) with stirring at 50° C., to thereby dissolve these ingredients. The thus-prepared solution was atomized by means of a spray dryer, to thereby yield the powder of a solid dispersion composition (average particle size: 26 $\mu$m).

Test Example 1

Dissolution Test

The solid dispersion compositions produced in Examples 1 and 2 and Comparative Examples 1 to 4 were confirmed in terms of the dissolvability of compound 1 and the dissolution stability, as follows.

Dissolution Test

Dissolution test 2 (paddle method), in accordance with general test methods (Japanese Pharmacopoeia).

A solid dispersion composition containing compound 1 (10 mg) was placed in water (900 mL), and the mixture was stirred at 37±1° C. and a paddle rotation speed of 50 r/min, to measure a concentration of compound 1 at each time of 5, 30, 60 and 120 minutes thereafter. The sample solution collected at each time was filtered using a cellulose acetate membrane filter with 0.45 μm pore size (DISMIC-25cs, product of Toyo Roshi), and the following results in Table 1 were obtained by HPLC using a reverse phase column (Inertsil ODS-2. product of GL Science).

TABLE 1

| Stirring time (min) | Examples | | Comparative Examples | | | | (w/v %) |
|---|---|---|---|---|---|---|---|
| | 1 | 2 | 1 | 2 | 3 | 4 | |
| 5 | 28.8 | 27.7 | 0.0 | 0.6 | 20.8 | 32.7 | |
| 30 | 34.1 | 34.9 | 0.0 | 1.0 | 21.6 | 27.4 | |
| 60 | 28.1 | 34.5 | 0.0 | 0.5 | 10.6 | 16.6 | |
| 120 | 20.0 | 23.7 | 0.0 | 0.0 | 1.3 | 1.6 | |

Thus, the dissolvability of compound 1 into water was little observed in the case of Comparative Example 1 where compound 1 was merely mixed with hydroxypropylmethyl cellulose and plyoxyethylene polyoxypropylene glycol, as well as in the case of Comparative Example 2 where a solid dispersion composition was prepared by mixing compound 1 with only hydroxypropylmethyl cellulose, not with polyoxyethylene polyoxypropylene glycol. In the cases of Comparative Examples 3 and 4 where solid dispersion compositions were prepared by adding thereto a surfactant of the other type, compound 1 was able to dissolve into water in early phase, but its concentration decreased sequentially. In the contrast with such cases, the solid dispersion compositions of Examples 1 and 2, which were prepared by mixing compound 1 with both hydroxypropylmethyl cellulose and polyoxyethylene polyoxypropylene glycol, were confirmed to have excellent dissolvability of compound 1 in water, and to enable compound 1 to keep a constant concentration sequentially.

Example 3

Granules of the solid dispersion composition produced in Example 1 (62 g), lactose (160 g), carmelose calcium (36 g), and light anhydrous silicic acid (2 g) were mixed, and the mixture was compressed by use of a tablet compress, to thereby obtain tablets (0.26 g/tablet, diameter: 8.5 mm). The obtained tablets showed the same dissolvability as that achieved by the solid dispersion granules of Example 1.

The solid dispersion composition of the present invention exhibits the excellent dissolvability of 2-benzyl-5-(4-chlorophenyl)-6-[4-(methylthio)phenyl]-2H-pyridazin-3-one in water and allows the concentration of this compound to keep constant sequentially, which is also superior in dissolution stability.

What is claimed is:

1. A solid dispersion composition containing 2-benzyl-5-(4-chlorophenyl)-6-[4-(methylthio)phenyl]-2H-pyridazin-3-one, hydroxypropylmethyl cellulose, and polyoxyethylene polyoxypropylene glycol.

2. A readily dissoluble pharmaceutical compositions comprising a solid dispersion composition containing 2-benzyl-5-(4-chlorophenyl)-6-[4-(methylthio)phenyl]-2H-pyridazin-3-one, hydroxypropylmethyl cellulose, and polyoxyethylene polyoxypropylene glycol and a pharmacologically acceptable carrier.

* * * * *